United States Patent [19]

Nyfeler

[11] 4,332,816
[45] Jun. 1, 1982

[54] FUNGICIDAL 3-(N-CARBONYLAMINO)-PYRROLIDINE-2,5-DIONES

[75] Inventor: Robert Nyfeler, Basel, Switzerland

[73] Assignee: Ciba-Geigy Corporation, Ardsley, N.Y.

[21] Appl. No.: 212,471

[22] Filed: Dec. 3, 1980

[30] Foreign Application Priority Data

Dec. 7, 1979 [CH] Switzerland .................. 10871/79

[51] Int. Cl.³ .................. A61K 31/40; C07D 207/416
[52] U.S. Cl. .................................. 424/274; 542/420; 548/546
[58] Field of Search .................. 260/326.44; 424/274; 542/420

[56] References Cited

U.S. PATENT DOCUMENTS 3,538,114  11/1970  Himmele et al. ............... 260/326.44
3,745,170   7/1973  Fujinami et al. ............... 260/326.44

FOREIGN PATENT DOCUMENTS 1559600  3/1969  France .

Primary Examiner—Jane T. Fan
Attorney, Agent, or Firm—Frederick H. Rabin; John P. Spitals

[57] ABSTRACT

Novel compounds of the formula

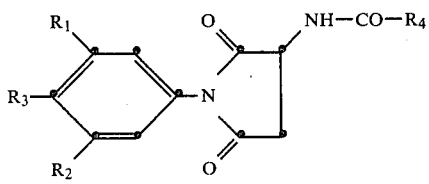

wherein $R_1$ is chlorine, bromine or nitro, $R_2$ is chlorine or bromine, $R_3$ is hydrogen or fluorine, $R_4$ is $C_1$–$C_9$alkyl which is unsubstituted or substituted by halogen or $C_1$–$C_3$alkoxy, or is $C_2$–$C_7$alkenyl, $C_2$–$C_4$alkynyl or $C_3$–$C_6$cycloalkyl, each of which is unsubstituted or substituted by halogen or aryl, or is phenyl which is unsubstituted or substituted by halogen, nitro or $C_1$–$C_4$alkyl, or is a 5-membered heterocyclic ring system which contains a hetero-atom, or is X-$R_5$, wherein X is oxygen or sulfur and $R_5$ is $C_1$–$C_6$alkyl or $C_3$–$C_6$alkenyl, each of which is unsubstituted or substituted by halogen or $C_1$–$C_3$alkoxy, or is phenyl which is unsubstituted or substituted by halogen, nitro, $C_1$–$C_3$alkyl or $C_1$–$C_3$alkoxy, or is benzyl which is unsubstituted or substituted by halogen or nitro.

These compounds possess useful microbicidal properties and can be used for controlling phytopathogenic microorganisms, especially phytopathogenic fungi. They have, for practical purposes, a very advantageous curative, preventive and systemic action for protecting cultivated plants, without adversely affecting these by undesirable side-effects.

21 Claims, No Drawings

FUNGICIDAL 3-(N-CARBONYLAMINO)-PYRROLIDINE-2,5-DIONES

The present invention relates to compounds of the formula I

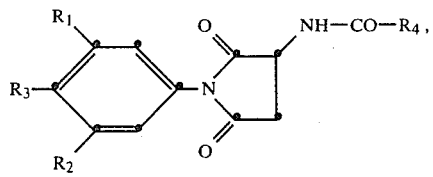

wherein $R_1$ is chlorine, bromine or nitro, $R_2$ is chlorine or bromine, $R_3$ is hydrogen or fluorine, $R_4$ is $C_1$–$C_9$alkyl which is unsubstituted or substituted by halogen or $C_1$–$C_3$alkoxy, or is $C_2$–$C_7$alkenyl, $C_2$–$C_4$alkynyl or $C_3$–$C_6$cycloalkyl, each of which is unsubstituted or substituted by halogen or aryl, or is phenyl which is unsubstituted or substituted by halogen, nitro or $C_1$–$C_4$alkyl, or is a 5-membered heterocyclic ring system which contains a hetero-atom, or is X-$R_5$, wherein X is oxygen or sulfur and $R_5$ is $C_1$–$C_6$alkyl or $C_3$–$C_6$alkenyl, each of which is unsubstituted or substituted by halogen or $C_1$–$C_3$alkoxy, or is phenyl which is unsubstituted or substituted by halogen, nitro, $C_1$–$C_3$alkyl or $C_1$–$C_3$alkoxy, or is benzyl which is unsubstituted or substituted by halogen or nitro.

Depending on the indicated number of carbon atoms, alkyl by itself or as moiety of another substituent denotes e.g. the following groups: methyl, ethyl, propyl, butyl, pentyl, hexyl or heptyl, as well as the isomers thereof, e.g. isopropyl, isobutyl, tert-butyl, isopentyl etc. Alkenyl is e.g. propen-1-yl, allyl, buten-1-yl, buten-2-yl, buten-3-yl etc., whilst alkynyl is e.g. ethynyl, propyn-1-yl, propargyl, butyn-1-yl etc. Throughout this specification, the term "halogen" denotes fluorine, chlorine, bromine or iodine, with chlorine or bromine being the preferred identities. Examples of 5-membered hetercyclic ring systems which contain a heteroatom are: tetrahydrofurane, furane, thiophene, tetrahydrothiophene, pyrrole, pyrrolidine, pyrroline etc.

The compounds of formula I fall into three main groups:
(a) compounds in which the radical $R_4$ is linked direct to the carbamide group=the carbamides,
(b) compounds in which the radical $R_5$ is linked through an oxygen atom to the carbamide group=the carbamates,
(c) compounds in which the radical $R_5$ is linked through a sulfur atom to the carbamide group=the thiocarbamates.

The compounds of formula I have a very advantageous microbicidal spectrum. They can be used e.g. against phytopathogenic microorganisms, especially against fungi.

Preferred microbicides of the formula I are those wherein
$R_1$ and $R_2$ are chlorine,
$R_3$ is hydrogen,
$R_4$ is $C_1$–$C_4$alkyl which is optionally substituted by halogen, $C_2$–$C_7$alkenyl which is optionally substituted by halogen or aryl, phenyl which is optionally substituted by halogen or $C_1$–$C_2$alkyl,
X is oxygen or sulfur, and
$R_5$ is $C_1$–$C_6$alkyl or $C_3$–$C_6$alkenyl, each of which is optionally substituted by halogen or $C_1$–$C_3$alkoxy, or phenyl which is optionally substituted by halogen or $C_1$–$C_3$alkyl.

A preferred group of microbicides comprises compounds of the formula I wherein $R_1$ and $R_2$ are chlorine and $R_4$ is $C_2$–$C_7$alkenyl which is optionally substituted by halogen or aryl.

A further preferred group of microbicides comprises compounds of the formula I wherein $R_1$ and $R_2$ are chlorine, $R_3$ is hydrogen, $R_4$ is —$OR_5$, wherein $R_5$ is $C_1$–$C_6$alkyl which is optionally be substituted by halogen or $C_1$–$C_3$alkoxy.

A third group of preferred microbicides comprises compounds of the formula I wherein $R_1$ and $R_2$ are chlorine, $R_3$ is hydrogen, and $R_4$ is —$SR_5$, wherein $R_5$ is $C_1$–$C_6$alkyl which is optionally substituted by halogen or $C_1$–$C_3$alkoxy.

In addition, the following individual compounds are especially preferred:
3-(N-methoxycarbonylamino)-1-(3,5-dichlorophenyl)-pyrrolidine-2,5-dione,
3-(N-ethoxycarbonylamino)-1-(3,5-dichlorophenyl)-pyrrolidine-2,5-dione,
3-(N-trifluoroacetylamino)-1-(3,5-dichlorophenyl)-pyrrolidine-2,5-dione,
3-[N-(2-methyl-1-propenyl)-carbonylamino]-1-(3,5-dichlorophenyl)-pyrrolidine-2,5-dione,
3-[N-(1,3-pentadienyl)-carbonylamino]-1-(3,5-dichlorophenyl)-pyrrolidine-2,5-dione,
3-(N-cyclopropylcarbonylamino)-1-(3,5-dichlorophenyl)-pyrrolidine-2,5-dione,
3-(N-isobutyloxycarbonylamino)-1-(3,5-dichlorophenyl)-pyrrolidine-2,5-dione,
3-[N-(2-propenyloxy)-carbonylamino]-1-(3,5-dichlorophenyl)-pyrrolidine-2,5-dione,
3-[N-(2-bromoethoxy)-carbonylamino]-1-(3,5-dichlorophenyl)-pyrrolidine-2,5-dione,
3-[N-(2-methoxyethoxy)-carbonylamino]-1-(3,5-dichlorophenyl)-pyrrolidine-2,5-dione,
3-(N-isopropylthiocarbonylamino)-1-(3,5-dichlorophenyl)-pyrrolidine-2,5-dione and
3-(N-ethylthiocarbonylamino)-1-(3,5-dichlorophenyl)-pyrrolidine-2,5-dione.

The compounds of formula I can be obtained as described in detail below. In formulae II, III, IV and V, the substituents $R_1$, $R_2$ and $R_3$ are as defined for formula I, $R_6$ is —NH—CO—$R_4$ or —$NHR_7$, wherein $R_4$ is as defined for formula I and $R_7$ is a protective group customary in peptide chemistry, e.g. benzoxycarbonyl, tertbutoxycarbonyl etc. Hal denotes halogen, e.g. fluorine, chlorine, bromine or iodine, especially chlorine or bromine.

The compounds of formula I are obtained by condensing a substituted aniline of the formula II with an aspartic acid derivative of the formula III

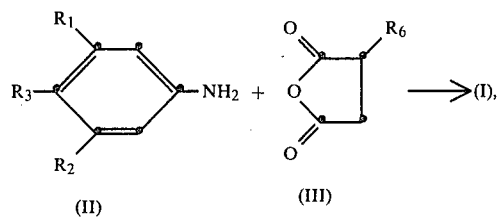

wherein R$_6$ is —NH—CO—R$_4$ or —NHR$_7$, and R$_1$, R$_2$, R$_3$ and R$_4$ are as defined for formula I, whilst R$_7$ is a protective group customarily employed in peptide chemistry, and, if R$_6$ is —NHR$_7$, the reaction proceeds via an intermediate of the formula IV

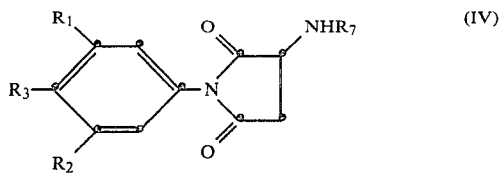

such that the protective group is split off in a manner known per se and the amino group reacts with a reactive carboxylic acid, or derivative thereof, in a subsequent N-acylation, to give the final product of the formula I.

The microbicides of the formula I are compounds which are stable in air, virtually insoluble in water and soluble in most common organic solvents, and are destroyed by strong alkalies and acids.

The condensation reaction (II+III) is conveniently carried out in an inert solvent under normal pressure. Examples of such solvents are: aromatic and aliphatic hydrocarbons such as benzene, toluene, xylenes, petroleum ether, ligroin or cyclohexane; halogenated hydrocarbons such as chlorobenzene, methylene chloride, ethylene chloride, chloroform, carbon tetrachloride or tetrachloroethylene; ethers and ethereal compounds such as diethyl either, diisopropyl ether, tert-butylmethyl ether, dimethoxy ethane, dioxane, tetrahydrofurane or anisole; esters such as ethyl acetate, propyl acetate or butyl acetate; or compounds such as dimethyl sulfoxide, dimethyl formamide, and mixtures of such solvents with one another.

The presence of a condensation agent can be advantageous in this reaction, e.g. a carboxylic acid anhydride such as acetic anhydride, propionic anhydride, or a compound such as acetyl chloride or thionyl chloride. The condensation agent can also act as solvent. Suitable condensation agents are also dicyclohexylcarbodiimide and molecular sieves.

This condensation reaction is accelerated by carrying it out e.g. in the temperature range from −10° to +150° C., preferably from 0° to +130° C. or at the boiling point of the solvent or solvent mixture. Sodium acetate can be added as catalyst.

As amino protective groups it is possible to use all the amino protective groups customary in peptide chemistry and which are comprehensively described in the appropriate reference works, e.g. in Houben-Weyl, Methoden der organischen Chemie, 4th edition, Vol. 15/I, E. Wünsch (editor): Synthese von Peptiden (Georg Thieme Verlag, Stuttgart, 1974). Preferred protective groups are groups which can be removed by acidolysis, such as preferably the tert-butoxycarbonyl group and analogous groups, e.g. tertamyloxycarbonyl, isopropyloxycarbonyl, diisopropylmethoxycarbonyl, allyloxycarbonyl, cyclopentyloxycarbonyl, cyclohexyloxycarbonyl, d-isobornyloxycarbonyl and adamantyloxycarbonyl, as well as groups of the aralkyl type such as benzhydryl and triphenylmethyl (trityl), or specific aralkoxycarbonyl groups of the 2-(p-biphenyl)-2-propyloxycarbonyl type, which are described in U.S. Pat. Nos. 3,875,207 and 3,944,590.

In addition, it is also possible to use amino protective groups which can be removed by reduction or under mild conditions in the presence of a base, e.g. in particular the benzyloxycarbonyl group and benxyloxycarbonyl groups which are substituted in the aromatic moiety by halogen atoms, nitro groups, lower alkoxy groups and/or lower alkyl radicals, such as the p-chloro- and p-bromobenzyloxycarbonyl group, p-nitrobenzyloxycarbonyl p-methoxybenzyloxycarbonyl group, p-tolyloxycarbonyl group, or else the isonicotinyloxycarbonyl group, and also acyl groups such as p-toluenesulfonyl, benzenesulfenyl, o-nitrobenzylsufenyl groups, or also formyl, trifluoroacetyl or phthaloyl groups.

A particularly advantageous amino protective group is an ethoxycarbonyl group which, in the β-position, carries a silyl group which is substituted by three hydrocarbon radicals, e.g. the triphenylsilyl, dimethylbutylsilyl or, preferably, trimethylsilyl group. A β-trihydrocarbylsilyl)ethoxycarbonyl group of this kind, such as a β-(trilower alkyl silyl)ethoxycarbonyl group, e.g. in particular the β-(trimethylsilyl)ethoxycarbonyl group, forms with the amino group to be protected a corresponding β-trihydrocarbylsilylethoxycarbonylamino group (e.g. the β-trimethylsilylethoxycarbonylamino group) which is resistant to the conditions of acid hydrolysis and hydrogenolysis, but which under very specific, very mild conditions, can be removed by the action of fluoride ions.

The removal of the protective group is accomplished in the usual manner known and employed in the art. The acid hydrolysis (acidolysis) is carried out e.g. with trifluoroacetic acid, hydrobromic acid, hydrochloric acid or hydrofluoric acid, and also in the case of protective groups which are sensitive to acid, with a lower aliphatic carboxylic acid such as formic acid and/or acetic acid, in the presence of water and, if desired, of a polyhalogenated lower alkanol or lower alkanone such as 1,1,1,3,3,3-hexafluoropropan-2-ol or hexafluoroacetone. The groups which can be removed by reduction, especially those which contain the benzyl radicals, are preferably removed by hydrogenolysis, e.g. by palladium-catalysed hydrogenation. The isonicotinyloxycarbonyl group is preferably removed by reduction with zinc.

The subsequent N-acylation is conveniently carried out in the customary inert organic solvents, preferably under mild conditions (−10° to +20° C.). Suitable acylating agents are reactive carboxylic acids or derivatives thereof, especially acid halides (e.g. acid chlorides and acid bromides), esters and anhydrides. In this reaction, it is advantageous to neutralise the liberated acid by means of a suitable acid acceptor. Suitable acid acceptors are e.g. organic bases such as trialkylamines (trimethylamine, triethylamine), pyridine and pyridine bases, or inorganic bases such as oxides, hydroxides, bicarbonates, carbonates or hydrides of alkali metals and alkaline earth metals. It is expedient to carry out the reaction in the presence of 2 equivalents of the acid acceptor (based on product I), using a 4-dialkylaminopyrdine as catalyst.

Substituted anilines of the formula II are generally known. The majority of the aspartic acid derivatives of the formula III are known and are obtained by methods which are known per se from the free aspartic acid, e.g. by acylation of the acid and subsequent intramolecular condensation (cf. Houben-Weyl, Vol. 15/2, page 219 ff). The compounds of the formula III can also be obtained by reaction of aspartic acid with an appropriate carboxylic acid anhydride [(cf. J. Med. Chem. 16, 163 (1973)].

In a variant of the above process, the compounds of formula I in which $R_4$ is a radical $-XR_5$, are obtained by reacting an aspartic acid derivative of the formula V, in the presence of 2 equivalents of an acid acceptor, with phosgene, and esterifying the resultant carbamoyl chloride of the formula VI, in the presence of 1 equivalent of an acide acceptor, with an alcohol or thioalcohol of the formula VII:

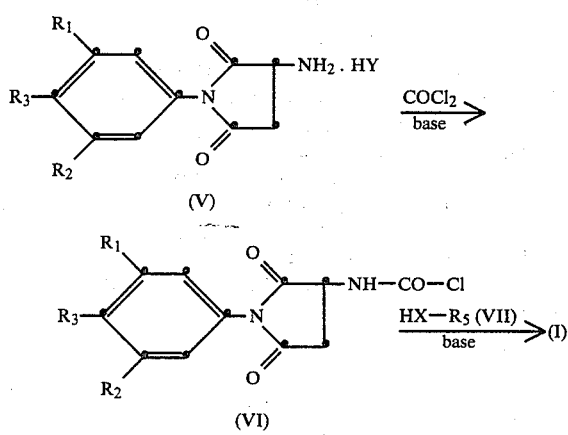

In the formulae V to VII, the substitutents $R_1$ to $R_3$ and X are as defined for formula I, and Y is halogen, especially chlorine or bromine.

The chlorocarbonylation reaction (V→VI) and the esterification (VI+VII→I) are conveniently carried out in solvents which are inert to the reactants. Suitable solvents are those indicated for the above condensation reaction.

Examples of acid acceptors are organic bases such as triethylamine, diethylamine, pyridine, 4-dimethylamino-pyridine, or inorganic bases such as sodium and potassium hydroxide, sodium and potassium carbonate, magnesium and calcium oxide.

The chlorocarbonylation is carried out in the temperature range from $-50°$ to $+50+$ C., with the preferred range being from $-40°$ to $-20°$ C. The subsequent esterification of the carbamoyl chloride to give compounds of the formula I is carried out in the temperature range from $-20°$ C. to the boiling point of the reaction mixture, with the preferred range being from $-10°$ to $+30°$ C.

The starting compounds of the formula V are obtained as hydrogen halides direct by removal of the protective group $R_7$ with hydrohalic acid from the intermediate of the formula IV of the main process.

The preparatory method in all its described variants constitutes an object of the invention.

The compounds of the formula I

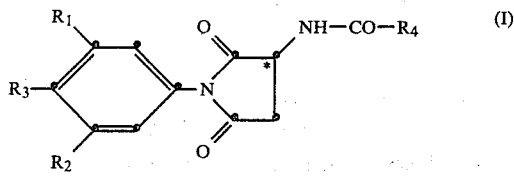

contain an asymmetrical carbon atom *C in the pyrrolidine ring adjacent to the side-chain and can be synthesised, in conventional manner, as pure optical antipodes of the product I, e.g. by starting from an enantiomeric form of aspartic acid. Depending on the substitution, further centres of asymmetry result. Compounds of the formula I also form different diastereoisomers.

The different isomers have different microbicidal properties. Provided a synthesis with the object of obtaining pure isomers is not carried out, a product of the formula I will always be obtained in the form of a mixture of these isomers.

Surprisingly, it has been found that compounds of the formula I possess, for practical purposes, a very useful microbicidal spectrum. They can be used, for example, for protecting cultivated plants.

The principal field of use of compounds of the formula I resides in the control of harmful microorganisms, especially phytopathogenic fungi. Accordingly, these compounds have a very useful curative and preventive action for protecting cultivated plants without adversely affecting these by undesirable side-effects. Examples of cultivated plants within the scope of this invention are: cereals (wheat, barley, rye, oats, rice), beet (sugar beet and fodder beet), drupes, pomes and soft fruit (apples, pears, plums, peaches, almonds, cherries, strawberries, rasberries and blackberries), leguminous plants (beans, lentils, peas, soybeans), oil plants (rape, mustard, poppy, olives, sunflowers, coconuts, castor oil plants, cocoa beans, ground nuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), or plants such as maize, tobacco, nuts, coffee, sugar cane, tea, vines, hops, bananas and natural rubber plants, as well as ornamentals.

With the compounds of the formula I it is possible to inhibit or destroy the microorganisms which occur in plants or parts of plants (fruit, blossoms, leaves, stems, tubers, roots) in these and also related crops of useful plants, and also to protect from attack by such microorganisms the parts of plants which grow later. The compounds of formula I are effective against the following phytopathogenic fungi: e.g. the Erysiphaceae belonging to the family of the Ascomycetes, and also fungi imperfecti such as Botrytis and Monilinia.

The compounds of the formula I can also be used as seed dressing agents for protecting seeds (fruit, tubers, grains) and plant cuttings from fungus infections and from microorganisms which occur in the soil.

Accordingly, the invention also relates to the use of compounds of the formula I for controlling phythopathogenic microorganisms and for the preventive treatment of plants to protect them from attack by such microorganisms.

For the control of such microorganisms, the compounds of formula I may be used as pure active ingredient or together with suitable carriers and/or adjuvants. Suitable carriers and adjuvants can be solid or liquid and correspond to the substances conventionally used in the art of formulation, for example natural or regenerated substances, solvents, dispersants, wetting agents, tackifiers, thickeners, binders and/or fertilisers. Compounds of the formula I can also be used in admixture with e.g. pesticides or preparations which promote plant growth. The concentration of active ingredient (compound of formula I) in commercial compositions is in general from 0.0001 to 90%.

In the following Examples, parts and percentages are by weight.

PREPARATORY EXAMPLES

Example 1

Preparation of

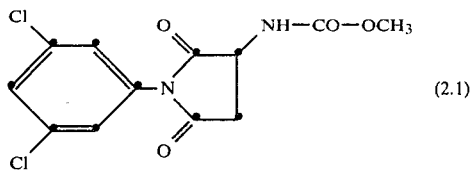

(2.1)

3-(N-methoxycarbonylamino)-1-(3,5-dichlorophenyl)-pyrrolidine-2,5-dione 12.9 g of N-methoxycarbonylaspartic anhydride are dissolved in 100 ml of tetrahydrofurane, and to this solution is added a solution of 12 g of 3,5-dichloroaniline in 50 ml of tetrahydrofurane. The reaction solution is stirred for 4 hours at 50° C. and then evaporated to dryness in vacuo. The residue is dissolved in 80 ml of acetic anhydride and then 2.5 g of sodium acetate are added and the solution is stirred for 1½ hours at 80° C. After cooling to room temperature, the reaction mixture is poured into water and stirred vigorously for ½ hour. The mixture is extracted with ethyl acetate and the extracts are washed successively with saturated sodium bicarbonate solution and saturated sodium chloride solution, then dried over sodium sulfate, filtered and concentrated. Recrystallisation of the residue affords colourless crystals of the above compound with a melting point of 136°–138° C.

EXAMPLE 2

(a) Preparation of an intermediate

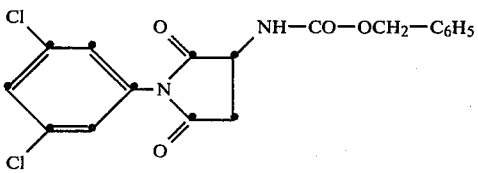

3-(N-benzyloxycarbonylamino)-1-(3,5-dichlorophenyl)-pyrrolidine-2,5-dione

A solution of 32 g of 3,5-dichloroaniline in 100 ml of tetrahydrofurane is added dropwise to a solutuion of 44 g of N-benzyloxycarbonylaminoaspartic anhydride in 200 ml of tetrahydrofurane. The reaction solution is stirred for 16 hours at room temperature and then evaporated to dryness. The residue is taken up in 200 ml of acetic anhydride and, after addition of 2.5 g of sodium acetate, the solution is stirred for 4 hours at 80° C. The reaction mixture is then cooled to room temperature, poured into water, and stirred vigorously for 30 minutes. The crystalline residue is collected by filtration, triturated with a small amount of cold water, filtered once more, washed thoroughly with water and dried in vacuo. The colourless crystals melt at 112°–113° C.

(b) Preparation of an intermediate

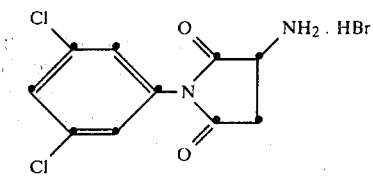

3-amino-1-(3,5-dichlorophenyl)-pyrrolidine-2,5-dione hydrobromide 85 g of 3-(N-benzyloxycarbonylamino)-1-(3,5-dichlorophenyl)pyrrolidine-2,5-dione are mixed with 200 ml of a solution of glacial acetic acid which is saturated with hydrobromic acid, and the mixture is then stirred for 1½ hours at room temperature. Then 1 liter of diethyl ether is added and the precipitated crystals are rapidly collected by filtration, washed with diethyl ether and dried over potassium hydroxide in vacuo. The hydrobromide is obtained in the form of colourless crystals which melt at 278°–280° C. with decomposition.

(c) Preparation of a final product

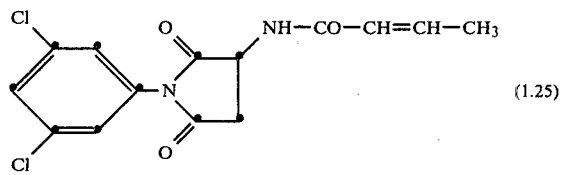

(1.25)

3-(N-crotylamino)-1-(3,5-dichlorophenyl)-pyrrolidine-2,5-dione

To 13.6 g of 3-amino-1-(3,5-dichlorophenyl)pyrrolidine-2,5-dione hydrobromide in 100 ml of tetrahydrofurane are added, at 0° C., 12 ml of triethylamine. Then 6 ml of crotonyl chloride are added dropwise and the reaction mixture is stirred for a further 12 hours at room temperature. The solution is then filtered and the filtrate is concentrated. The residue is purified by column chromatography over silica gel with dichloromethane/petroleum ether (85:15) as eluant. The solvent is removed and the residue is recrystallised from ethyl acetate/petroleum ether. The colourless crystals melt at 107°–110° C.

Example 3

Preparation of

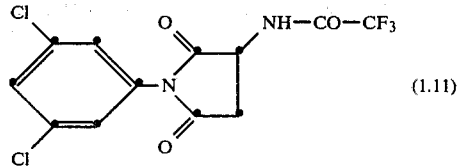

(1.11)

3-(N-trifluoroacetylamine)-1-(3,5-dichlorophenyl)-pyrrolidine-2,5-dione

A solution of 30 g of 3,5-dichloroaniline in 100 ml of tetrahydrofurane is added dropwise at room temperature to a solution of 40 g of trifluoroacetylaspartic anhydride in 100 ml of tetrahydrofurane. The reaction mixture is stirred for 16 hours at 50° C. and then concentrated. The crystalline residue is stirred for 2 hours at 50° C. in 150 ml of acetic anhydride together with 3 g of sodium acetate. The solution is then poured into water and stirred for 1½ hours. The precipitate is collected by filtration, washed with water, dried, and recrystallised from ethyl acetate/petroleum ether. The colourless crystals obtained have a melting point of 147°–148° C.

Example 4

(a) Preparation of an intermediate

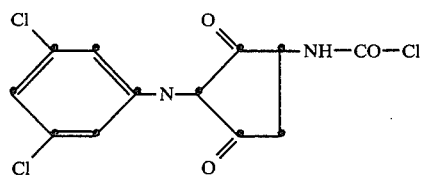

3-(N-chlorocarbonylamino)-1-(3,5-dichlorophenyl)-pyrrolidine-2,5-dione

After dilution with 200 ml of tetrahydrofurane, 34 g of 3-amino-1-(3,5-dichlorophenyl)pyrrolidine-2,5-dione hydrobromide (obtained in Example 2b) are added at −20° C. to 104 ml of a 20% solution of phosgene in toluene. Then 27.9 g of triethylamine in 100 ml of tetrahydrofurane are added dropwise at −37° to −28° C. and the reaction mixture is thereafter stirred for a further 12 hours at −33° C. to bring the reaction to completion. The precipitate is collected by filtration at −20° C. and the solution is concentrated. The 3-(N-chlorocarbonylamino)-1-(3,5-dichlorophenyl)pyrrolidine-2,5-dione obtained is used direct for the consequent reaction.

(b) Preparation of

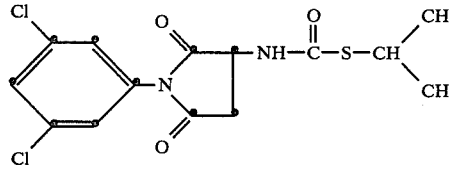

3-(N-isopropylthiocarbonylamino)-1-(3,5-dichlorophenyl)-pyrrolidine-2,5-dione

A solution of the 3-(N-chlorocarbonylamino)-1-(3,5-dichlorophenyl)pyrrolidine-2,5-dione obtained in (a), in 100 ml of tetrahydrofurane, is added slowly dropwise to a solution, cooled to −5° C., of 0.3 g of 4-dimethylaminopyridine, 30.7 ml of triethylamine and 20.6 ml of isopropylmercaptan in 200 ml of tetrahydrofurane. The reaction mixture is stirred for 12 hours at room temperature and the precipitate is collected by filtration. The filtrate is concentrated and the residue is crystallised from isopropanol. The colourless final product is crystallised with 1 molecular equivalent of isopropanol and has a melting point of 161°–163° C.

The following final products of the formula I are prepared in similar manner:

TABLE 1

Compounds of the formula I

| Compound | $R_1$ | $R_2$ | $R_3$ | $R_4$ | Physical data |
|---|---|---|---|---|---|
| 1.1 | Cl | Cl | H | —$CH_3$ | m.p. 140–142° C. |
| 1.2 | Cl | Cl | H | —$CH_2Cl$ | m.p. 140–142° C. |
| 1.3 | Cl | Cl | H | —$CH_2Br$ | m.p. 143–145° C. |
| 1.4 | Cl | Cl | H | —$CH_2I$ | m.p. 169–172° C. |
| 1.5 | Cl | Cl | H | —$CHCl_2$ | |
| 1.6 | Cl | Cl | H | —$CCl_3$ | |
| 1.7 | Br | Br | H | —$CH_3$ | |
| 1.8 | Br | Br | H | —$CH_2Br$ | |
| 1.9 | Cl | Cl | F | —$CH_3$ | |
| 1.10 | Br | Br | F | —$CF_3$ | |
| 1.11 | Cl | Cl | H | —$CF_3$ | m.p. 147–148° C. |
| 1.12 | Cl | Cl | H | —$C_2H_5$ | |
| 1.13 | Cl | Cl | H | —$C_3H_7$—n | m.p. 127–129° C. |
| 1.14 | Cl | Cl | H | —$C_7H_{15}$—n | |
| 1.15 | Cl | Cl | H | —$C_2Cl_5$ | |
| 1.16 | Br | Br | H | —$C_4H_9$—n | |
| 1.17 | Br | Br | F | —$C_2H_5$ | |
| 1.18 | Cl | Cl | H | cyclopropyl | m.p. 162–164° C. |
| 1.19 | Cl | Cl | F | cyclopropyl | |
| 1.20 | Cl | Cl | H | cyclohexyl | m.p. 175–176° C. |
| 1.21 | Cl | Cl | H | —$CH=CH_2$ | m.p. 153–155° C. |
| 1.22 | Cl | Cl | H | —$CCl=CCl_2$ | m.p. 136–138° C. |
| 1.23 | Br | Br | H | —$CH=CH_2$ | |
| 1.24 | Cl | Cl | F | —$CH=CH_2$ | |
| 1.25 | Cl | Cl | H | —$CH=CH—CH_3$ | m.p. 107–110° C. |
| 1.26 | Cl | Cl | H | —$CH=C(CH_3)_2$ | amorphous |
| 1.27 | Cl | Cl | H | —$(CH=CH)_2CH_3$ | m.p. 184–186° C. |
| 1.28 | Br | Br | H | —$CH=C(CH_3)_2$ | |
| 1.29 | Cl | Cl | F | —$CH=C(CH_3)_2$ | |
| 1.30 | Cl | Cl | H | —$C(CH_3)=CH—CH_3$ | m.p. 47–48° C. |
| 1.31 | Cl | Cl | F | —$C(CH_3)=CH_2$ | |
| 1.32 | $NO_2$ | Cl | H | —$CH=CH—C_6H_5$ | |
| 1.33 | Cl | Cl | F | —$C(CH_3)=CH_2$ | |
| 1.34 | Cl | Cl | F | —$C(CH_3)=C(CH_3)_2$ | |
| 1.35 | Cl | Cl | H | —$CH=C(C_2H_5)_2$ | |
| 1.36 | Cl | Cl | H | —$C(C_2H_5)=CH_2$ | |
| 1.37 | Cl | Cl | H | furyl | resin |
| 1.38 | Cl | Cl | F | tetrahydrofuryl | |
| 1.39 | Cl | Cl | H | pyrrolyl | |
| 1.40 | $NO_2$ | Cl | H | —$C_6H_5$ | |
| 1.41 | Cl | Cl | F | —$C_6H_5$ | |
| 1.42 | Cl | Cl | H | —$C_6H_3Cl_2(3,4)$ | |
| 1.43 | Cl | Cl | F | —$C_6H_3Cl_2(2,5)$ | |
| 1.44 | Cl | Cl | H | —$(CH_2)_8CH_3$ | m.p. 85–88° C. |
| 1.45 | Cl | Cl | H | —$CH_2OC_3H_7$—n | |
| 1.46 | Cl | Cl | F | —$CH_2OC_2H_5$ | |
| 1.47 | Br | Br | H | —$CH_2OC_3H_7$—i | |
| 1.48 | Cl | Cl | H | —$CH_2OCH_3$ | m.p. 157–172° C. |
| 1.49 | Cl | Cl | H | —$C_6H_4CH_3(2)$ | |
| 1.50 | Cl | Cl | H | —$C_6H_3(CH_3)_2(3,4)$ | |
| 1.51 | $NO_2$ | Cl | H | —$CH=CH_2$ | |
| 1.52 | $NO_2$ | Cl | H | —$C_3H_7$—n | |
| 1.53 | Cl | Cl | H | —$CH=CH—C_6H_5$ | m.p. 174–175° C. |
| 1.54 | Cl | Cl | H | —$C(CH_3)=CH_2$ | m.p. 125–128° C. |
| 1.55 | Cl | Cl | H | —$C_3H_7$—i | m.p. 160–161° C. |
| 1.56 | Cl | Cl | H | —$C(CH_3)_3$ | m.p. 185–188° C. |

TABLE 2

Compounds of the formula I

| Compound | $R_1$ | $R_2$ | $R_3$ | —X—$R_5$ | Physical data |
|---|---|---|---|---|---|
| 2.1 | Cl | Cl | H | —$OCH_3$ | m.p. 136–138° C. |
| 2.2 | Br | Br | H | —$OCH_3$ | |
| 2.3 | Cl | Cl | H | —S—$CH_2$—CH=$CH_2$ | wax-like |
| 2.4 | Cl | Cl | H | —$SCH_3$(x i-$C_3H_7OH$) | m.p. 73–76° C. |
| 2.5 | Cl | Cl | H | —$OC_2H_5$ | m.p. 67–69° C. |
| 2.6 | Cl | Cl | H | —$SC_2H_5$ | m.p. 118–123° C. |
| 2.7 | Cl | Cl | F | —$OCH_2$—$CH_3$ | |
| 2.8 | Cl | Cl | H | —$OCH_2$—$C_3H_7$—i | m.p. 152–155° C. |
| 2.9 | Br | Br | H | —$OCH_2$—$C_6H_5$ | |

TABLE 2-continued

| | Compounds of the formula I | | | | |
|---|---|---|---|---|---|
| Compound | $R_1$ | $R_2$ | $R_3$ | $-X-R_5$ | Physical data |
| 2.10 | $NO_2$ | Cl | H | $-OCH_3$ | |
| 2.11 | Cl | Cl | H | $-OCH_2-C_6H_5$ | m.p. 112–113° C. |
| 2.12 | Cl | Cl | H | $-O-CH_2-CH_2-OCH_3$ | m.p. 109–110° C. |
| 2.13 | $NO_2$ | Cl | H | $-OC_3H_7-n$ | |
| 2.14 | Cl | Cl | H | $-OCH_2CH=CH_2$ | m.p. 56–58° C. |
| 2.15 | Cl | Cl | H | $-O-CH_2-CH_2-Br$ | m.p. 131–134° C. |
| 2.16 | Br | Br | H | $-O-CH_2-CCl_3$ | |
| 2.17 | Cl | Cl | H | $-O-CH_2-CCl_3$ | sinters from 80° C. |
| 2.18 | Cl | Cl | H | $-S-C_3H_7-i(x\ i-C_3H_7OH)$ | m.p. 161–163° C. |
| 2.19 | Cl | Cl | H | $-OC_6H_5$ | |
| 2.20 | Br | Br | H | $-OC_6H_5$ | |
| 2.21 | Cl | Cl | H | $-S-C_4H_9-n$ | m.p. 99–104° C. |
| 2.22 | Cl | Cl | H | $-OC_6H_3(CH_3)_2(2,6)$ | |
| 2.23 | Cl | Cl | H | $-SC_6H_5$ | |
| 2.24 | Cl | Cl | F | $-SCH_2C_6H_5$ | |
| 2.25 | Cl | Cl | H | $-OCH_2C_6H_3(CH_3)_2(2,6)$ | |
| 2.26 | Cl | Cl | F | $-SC_3H_7-i$ | |
| 2.27 | Br | Br | H | $-SCH_3$ | |
| 2.28 | Cl | Cl | H | $-S-C(CH_3)_3$ | m.p. 174–182° C. |

For application, the compounds of the formula I can be processed to the following formulations:

FORMULATION EXAMPLES

Example 4

Solid formulations:

Dusts and tracking powders contain in general up to 10% of active ingredient. A 5% dust can consist for example of 5 parts of active ingredient and 95 parts of an adjuvant, such as talcum; and a 2% dust of 2 parts of active ingredient, 1 part of highly dispersed silica and 97 parts of talcum. Further mixtures with these and other carriers and adjuvants commonly employed in the art of formulation are also possible. These dusts and tracking powders are produced by mixing and grinding the active ingredients with the carriers and adjuvants, and can be applied in this form by dusting.

Granulates, such as coated, impregnated and homogeneous granulates and also pellets, usually contain 1 to 80% of active ingredient. A 5% granulate can thus be composed of e.g. 5 parts of active ingredient, 0.25 part of epoxidised vegetable oil, 0.25 part of cetyl polyglycol ether, 3.50 parts of polyethylene glycol and 91 parts of kaolin (preferred particle size 0.3–0.8 mm). The granulate can be prepared as follows: The active ingredient is mixed with the vegetable oil, the mixture is dissolved in 6 parts of acetone, and the polyethylene glycol and cetyl polyglycol ether are added. The solution obtained is sprayed onto kaolin, and the acetone is subsequently evaporated off in vacuo. A microgranulate of this type is advantageously used for controlling soil fungi.

Example 5

Liquid formulations:

A distinction is generally made between active ingredient concentrates which are dispersible or soluble in water, and aerosols. Active ingredient concentrates dispersible in water include e.g. wettable powders and pastes, which usually contain 25–90% of active ingredient in commercial packs, and 0.01 to 15% of active ingredient in ready-for-use solutions. Emulsifiable concentrates contain 10 to 50% of active ingredient, and solution concentrates contain in ready-for-use solution 0.001 to 20% of active ingredient. A 70% wettable powder can thus be composed of e.g. 70 parts of active ingredient, 5 parts of sodium dibutylnaphthalene sulfonate, 3 parts of naphthalenesulfonic acid/phenolsulfonic acid/formaldehyde condensate (in the ratio of 3:2:1), 10 parts of kaolin and 12 parts of chalk, for example Champagne chalk. A 40% wettable powder can consist e.g. of the following substances: 40 parts of active ingredient, 5 parts of sodium lignosulfonate, 1 part of sodium dibutylnaphthalenesulfonate and 54 parts of silicic acid. A 25% wettable powder can be formulated in different ways. It can be composed e.g. of: 25 parts of active ingredient, 4.5 parts of calcium lignosulfonate, 1.9 parts of chalk, for example a mixture of Champagne chalk/hydroxyethylene cellulose (1:1), 1.5 parts of sodium dibutylnaphthalenesulfonate, 19.5 parts of silicic acid, 19.5 parts of Champagne chalk and 28.1 parts of kaolin. A 25% wettable powder can also consist of e.g.: 25 parts of active ingredient, 2.5 parts of isooctylphenoxypolyoxyethylene-ethanol, 1.7 parts of a mixture of Champagne chalk/hydroxyethyl cellulose (1:1), 8.3 parts of sodium silicate, 16.5 parts of kieselguhr and 46 parts of kaolin. A 10% wettable powder can be formulated e.g. from: 10 parts of active ingredient, 3 parts of a mixture of the sodium salts of saturated fatty alcohol sulfonates, 5 parts of naphthalenesulfonic acid/formaldehyde condensate and 82 parts of kaolin. Other wettable powders can be formulated as mixtures of 5 to 30% of active ingredient together with 5 parts of an absorbent carrier material, such as silicic acid, 55 to 80 parts of a carrier such as kaolin, and a dispersing agent mixture consisting of 5 parts of sodium arylsulfonate and 5 parts of an alkylaryl polyglycol ether. A 25% emulsifiable concentrate can contain e.g. the following emulsifiable substances: 25 parts of active ingredient, 2.5 parts of epoxidised vegetable oil, 10 parts of a mixture of an alkylarylsulfonate and a fatty alcohol polyglycol ether, 5 parts of dimethyl formamide and 57.5 parts of xylene. Emulsions of the desired concentration can be prepared from such concentrates by dilution with water. These emulsions are particularly suitable for leaf application. It is, moreover, possible to produce further wettable powders having other mixture ratios and containing other carriers and adjuvants customarily employed in formulation technology. The active ingredients are intimately mixed in suitable mixers with the stated adjuvants, and subsequently ground on the appropriate mills and rollers. Wettable powders having excellent wetting and suspension properties are obtained: These wettable powders can be diluted with water to obtain suspensions of the desired concentration, and are particularly suitable for leaf application. The invention also relates to such compositions.

Compositions which contain, as described above, as active ingredient, a compound of the formula I, for example compounds 1.1, 1.2, 1.3, 1.4, 1.11, 1.13, 1.18, 1.20, 1.21, 1.22, 1.25, 1.26, 1.27, 1.30, 1.37, 1.42, 1.44, 1.48, 1.53, 1.54, 1.55, 1.56, 2.1, 2.3, 2.4, 2.5, 2.6, 2.8, 2.11, 2.12, 2.14, 2.15, 2.17, 2.18, 2.21 and 2.28, can be used very successfully against harmful microorganisms, especially against leaf, soil and seed fungi, when these compositions are applied e.g. in the form of a wettable powder. Compositions which contain, as active ingredient, one of the other compounds of Tables I and II, can also be used with equally good or similar success.

BIOLOGICAL EXAMPLES

Example 6

Action against Erysiphe graminis on barley (a) Residual protective action
Barley plants about 8 cm in height are sprayed with a spray mixture (0.02% of active ingredient) prepared from the active ingredient formulated on a wettable powder. The treated plants are dusted with conidia of the fungus after 3-4 hours. The infected barley plants are then stood in a greenhouse at about 22° C. The extent of the fungus infection is evaluated after 10 days.

(b) Systemic action
Barley plants about 8 cm in height are treated with a spray mixture (0.006% of active ingredient, based on the volume of the soil) prepared from the active ingredient formulated as wettable powder. Care is taken that the spray mixture does not come in contact with the parts of the plants above the soil. The treated plants are infected 48 hours later with a conidia suspension of the fungus. The infected barley plants are then stood in a greenhouse at about 22° C. and the extent of the fungus infection is evaluated after 10 days.

In the treatment of barley plants against Erysiphe fungi with compounds of the formula I, e.g. compounds 1.4, 1.11, 1.18, 1.54, 2.1 and 2.5, the fungus attack was reduced to less than 10% in comparison to control plants. Moreover, compound 1.14 had additionally a systemic action.

Example 7

Residual protective action against Botrytis cinerea on beans

Bean plants about 10 cm in height are sprayed with a spray mixture (0.02% of active ingredient) prepared from the active ingredient formulated as wettable powder. After 48 hours, the treated plants are infected with a conidia suspension of the fungus. The infected plants are incubated for 3 days at 95-100% relative humidity and 21° C., and evaluation of the fungus attack is then made.

In contrast to untreated control plants (100% attack), only 5% of the bean plants treated with a wettable powder containing, as active ingredient, one of compounds 1.2, 1.3, 1.4, 1.18, 1.25, 1.26, 1.27, 2.1, 2.3, 2.5, 2.8, 2.14, 2.15 or 2.18, are attacked.

Example 8

Action against Monilinia on plant blossoms

Individual plum branches in full blossom are sprayed with a wettable powder (0.025% of active ingredient) prepared from an emulsifiable concentrate. A few hours later, the inflorescences are cut off, put with the stem into the wet bottom of plastic dishes, and inoculated with a spore suspension. The dishes are then covered loosely with transparent plastic sheeting and kept for 2 days at room temperature. A count of infected blossoms is made to determine the extent of the attack, using 40 blossoms per compound. Reduction of attack to less than 20% is effected with compounds 1.26, 1.27 and 2.1. Compound 2.1 inhibited attack completely.

What is claimed is:
1. A compound of the formula

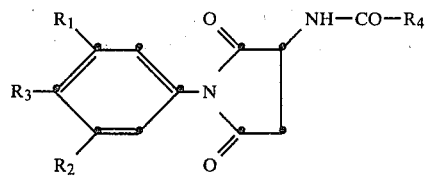

wherein $R_1$ is chlorine, bromine or nitro, $R_2$ is chlorine or bromine, $R_3$ is hydrogen or fluorine, $R_4$ is $C_1$-$C_9$alkyl which is unsubstituted or substituted by halogen or $C_1$-$C_3$alkoxy, or is $C_2$-$C_7$alkenyl, $C_2$-$C_4$alkynyl or $C_3$-$C_6$cycloalkyl, each of which is unsubstituted or substituted by halogen or phenyl, phenyl which is unsubstituted or substituted by halogen, nitro or $C_1$-$C_4$alkyl, or is X—$R_5$, wherein X is oxygen or sulfur and $R_5$ is $C_1$-$C_6$alkyl or $C_3$-$C_6$alkenyl, each of which is unsubstituted or substituted by halogen or $C_1$-$C_3$alkoxy, or is phenyl which is unsubstituted or substituted by halogen, nitro, $C_1$-$C_3$alkyl or $C_1$-$C_3$alkoxy, or is benzyl which is unsubstituted or substituted by halogen or nitro.

2. A compound according to claim 1, wherein $R_1$ and $R_2$ are chlorine, $R_3$ is hydrogen, $R_4$ is $C_1$-$C_4$alkyl which is optionally substituted by halogen, $C_2$-$C_7$alkenyl which is optionally substituted by halogen or phenyl, phenyl which is optionally substituted by halogen or $C_1$-$C_2$alkyl, or is X-$R_5$, wherein X is oxygen or sulfur, and $R_5$ is $C_1$-$C_6$alkyl or $C_3$-$C_6$alkenyl, each of which is optionally substituted by halogen or $C_1$-$C_3$alkoxy, or phenyl which is optionally substituted by halogen or $C_1$-$C_3$alkyl.

3. A compound according to claim 1, wherein $R_1$ and $R_2$ are chlorine and $R_4$ is $C_2$-$C_7$alkenyl which is optionally substituted by halogen or phenyl.

4. A compound according to claim 2, wherein $R_4$ is —$OR_5$, wherein $R_5$ is $C_1$-$C_6$alkyl which is optionally substituted by halogen or $C_1$-$C_3$alkoxy.

5. A compound according to claim 2, wherein $R_4$ is —$SR_5$, wherein $R_5$ is $C_1$-$C_6$alkyl which is optionally substituted by halogen or $C_1$-$C_3$alkoxy.

6. 3-(N-methoxycarbonylamino)-1-(3,5-dichlorophenyl)-pyrrolidine-3,5-dione according to claim 4.

7. 3-(N-ethoxycarbonylamino)-1-(3,5-dichlorophenyl)-pyrrolidine-2,5-dione according to claim 4.

8. 3-(N-trifluoroacetylamino)-1-(3,5-dichlorophenyl)-pyrrolidine-2,5-dione according to claim 2.

9. 3-[N-(2-methyl-1-propenyl)-carbonylamino]-1-(3,5-dichlorophenyl)-pyrrolidine-2,5-dione according to claim 3.

10. 3-[N-(1,3-pentadienyl)-carbonylamino]-1-(3,5-dichlorophenyl)-pyrrolidine-2,5-dione according to claim 3.

11. 3-(N-cyclopropylcarbonylamino)-1-(3,5-dichlorophenyl)-pyrrolidine-2,5-dione according to claim 1.

12. 3-(N-isobutyloxycarbonylamino)-1-(3,5-dichlorophenyl)-pyrrolidine-2,5-dione according to claim 4.

13. 3-[N-(2-propenyloxycarbonylamino]-1-(3,5-dichlorophenyl)-pyrrolidine-2,5-dione according to claim 1.

14. 3-[N-(2-bromoethoxy)carbonylamino]-1-(3,5-dichlorophenyl)-pyrrolidine-2,5-dione according to claim 4.

15. 3-[N-(2-methoxyethoxy)carbonylamino]-1-(3,5-dichlorophenyl)-pyrrolidine-2,5-dione according to claim 4.

16. 3-(N-isopropylthiocarbonylamino)-1-(3,5-dichlorophenyl)-pyrrolidine-2,5-dione according to claim 5.

17. 3-(N-ethylthiocarbonylamino)-1-(3,5-dichlorophenyl)-pyrrolidine-2,5-dione according to claim 5.

18. A composition for controlling or preventing attack by phytopathogenic microorganisms, which composition contains, as active component, of a microbicidally effective amount a compound according to claim 1, together with a carrier.

19. A method of controlling or preventing attack by phytopathogenic microorganisms at a locus, which comprises applying to said locus a microbicidally effective amount of a compound according to claim 1.

20. A method according to claim 19, wherein the microorganisms to be controlled are phytopathogenic fungi.

21. A method according to claim 20, wherein the fungi to be controlled are Ascomycetes or fungi imperfecti.

* * * * *